United States Patent [19]

Muentener et al.

[11] Patent Number: 5,213,293

[45] Date of Patent: May 25, 1993

[54] STAND EQUIPPED WITH ACCESSORY DEVICES FOR SUPPORTING A FREELY ORIENTABLE APPARATUS

[75] Inventors: Juerg Muentener; Otto Geschwentner; Juergen Metz, all of Balgach, Switzerland

[73] Assignee: Leica Heerbrugg AG, Heerbrugg, Switzerland

[21] Appl. No.: 681,503

[22] PCT Filed: Jul. 4, 1990

[86] PCT No.: PCT/EP90/01075

§ 371 Date: Apr. 24, 1991

§ 102(e) Date: Apr. 24, 1991

[87] PCT Pub. No.: WO91/00472

PCT Pub. Date: Jan. 10, 1991

[30] Foreign Application Priority Data

Jul. 4, 1989 [DE] Fed. Rep. of Germany ....... 3921857

[51] Int. Cl.$^5$ ................................................. F16L 3/00
[52] U.S. Cl. ......................... 248/123.1; 248/124; 248/162.1; 248/281.1; 248/585
[58] Field of Search ............... 248/123.1, 124, 162.1, 248/281.1, 282, 284, 585

[56] References Cited

U.S. PATENT DOCUMENTS

| 3,376,007 | 4/1968 | Chesterley | 248/282 |
|---|---|---|---|
| 4,166,602 | 9/1979 | Nilsen et al. | 248/123.1 X |
| 4,208,028 | 6/1980 | Brown et al. | 248/123.1 X |
| 4,344,595 | 8/1982 | Heller et al. | 248/123.1 X |

FOREIGN PATENT DOCUMENTS

| 0023003 | 1/1981 | European Pat. Off. . |
|---|---|---|
| 0023004 | 1/1981 | European Pat. Off. . |
| 0048404 | 3/1982 | European Pat. Off. . |
| 3728527 | 3/1988 | Fed. Rep. of Germany . |
| 8909957 | 2/1990 | Fed. Rep. of Germany . |
| 2074337 | 10/1981 | United Kingdom . |
| 2176764 | 1/1987 | United Kingdom . |

OTHER PUBLICATIONS

Zeiss brochure W 30–082–d of May 1988.
Wild Company brochure, Vl. 89 of Nov. 1986.

Primary Examiner—Ramon O. Ramirez
Attorney, Agent, or Firm—Foley & Lardner

[57] ABSTRACT

A stand for supporting an apparatus includes a main frame; a linkage parallelogram connected to the main frame; a first supporting arm connected to the linkage parallelogram; an energy storing element connected to the linkage parallelogram at a plurality of places; and a device for displacing the center of gravity of the apparatus. The displacing device includes a second supporting arm having a first non-vertical axis (A—A). The second supporting arm is rotatably connected to the first supporting arm and is connected to the apparatus by a connection point having a second non-vertical axis which is perpendicular to the first non-vertical axis. The displacing device displaces the center of gravity of the apparatus into a point of intersection of the first non-vertical axis and the second non-vertical axis.

10 Claims, 4 Drawing Sheets

STAND EQUIPPED WITH ACCESSORY DEVICES FOR SUPPORTING A FREELY ORIENTABLE APPARATUS

BACKGROUND OF THE INVENTION

1. Field of the Invention

The invention relates to accessory devices on a stand for apparatuses, especially operating microscopes, which are freely movable within a predetermined space and are freely orientable with respect to their position and their allocation to an object within this space. Such requirements are specifically placed on operating microscopes which are employed in ENT surgery; however, they are used to an increased extent also in the field of neurosurgery and of plastic surgery. Depending upon the respective field of application and the selected set object, it is possible to attach to the actual operating microscope various accessory modules such as an additional observation tube, a photographic connection, a camera etc., in a known manner. In this case, the calibration problems appertaining to the actual observation apparatus (microscope) which do indeed already exist are intensified.

2. Description of the Related Art

EP-A-23,003 discloses a supporting device for an optical observation apparatus in which a plurality of pivotal systems designed as linkage parallelograms permit the mobility of the microscope. In this case, use is made of a displaceable counterbalancing weight for free orientation in space. Moreover, electromagnetic retarder bearings ensure the fixing of the optimal stand setting.

EP-A-23,004 contains a description of an accessory device which is in particular capable of compensating rotational and tilting moments in that the position of the center of gravity of the microscope together with its accessories can be determined, and the equilibrium can be adjusted in accordance therewith.

EP-A-49,261 shows a support for an optical apparatus which exhibits as supporting device a rod system which extends through a ball bearing. The apparatus is secured to one of the ends (the lower end), and a counterbalancing weight is secured to the other (upper) end in such a manner that it is displaceable about three mutually perpendicular axes. This displaceable counterbalancing weight permits a free orientation of the microscope in space.

DE-OS-3,617,751 discloses a microscope unit in which an adjustable counterbalancing weight is used, which permits a balancing of the moment which is created about pivotal and tilting axes and which results from the addition or removal of components or modules.

Furthermore, the Wild company brochure (operating instructions) M2-690-XI.86 of November 1986 discloses an operating microscope stand in which the fine adjustment, i.e. the pivoting and inclination of the microscope, is possible by means of milled knobs and inclination levers on drive linkages.

Finally, the Zeiss brochure W 30-082-d of May 1988 ("Ground stand S 21") discloses the concept of providing, in the case of a linkage arm consisting of supporting arm and spring arm, a weight adjustment accessible from outside for the microscope equipment as well as brakes for an individual setting of the mobility of the linkages and of the upward/downward movement.

The described prior art exhibits the following disadvantages, individually or in combination. An essential disadvantage of all known solutions consists in that the resistance to motion of the pivot arms, even when it is adjustable, necessitates the exertion of a very large force for the upward or downward movement of the microscope. The consequence of this exertion of a large force is that a very precise orientation of the microscope in height is not possible without the additional operation of a focusing drive. This additional operation, in turn, involves an interruption of the work to be carried out under the microscope—for example microsurgery. It can be clearly seen without further ado that delays or interruptions of this type cause great disturbance or are dangerous. A further essential disadvantage of the exertion of this large force is that &:he operator, who himself performs very delicate work, may as a result of the exertion of force to be implemented by him undergo muscular stresses which inhibit or have a disadvantageous effect on the progress of the micro-operation. In quite general terms, it can be stated that an interruption of the operating procedure is involved if the operation must be interrupted for the purpose of an alteration of orientation of the optical apparatus, since, for example, the milled knobs must be operated.

Disadvantages of the aforementioned EP-A-23,003 arise from the required effort which arises upon the exchange of one apparatus for another which has a different weight. This effort is further increased in that the location of the position of the center of gravity and the setting of equilibrium cannot be implemented easily in logical terms and cannot be carried out without complications. Complicated, time-consulting equilibrium settings, which moreover cannot easily be implemented from the point of view of the operating personnel, impede a high degree of flexibility regarding accessories, which nowadays is to be required in modern operating microscopy.

SUMMARY OF THE INVENTION

It is accordingly the object of the present invention to provide accessory devices for a stand, to receive, for example, a microscope, this stand permitting an easy-action orientation of the apparatus, especially in height. In this case, it is additionally to be ensured that any alteration of position of the microscope during the operation does not lead to any disturbing interruption of that operation. Moreover, the object consists in designing the resettings of the equilibrium of the overall system which arise in the case of any change of the most widely varying accessory components for the microscope in a manner which is logical per se and capable of rapid execution. Finally, the object of the present invention consists in performing the calibration of the apparatus (microscope) together with its accessories without displacement of a counterbalancing weight, i.e. without onerous determination of the position of the center of gravity of the microscope together with its accessories.

The above objects are met by providing a stand for supporting an apparatus having a main frame, a linkage parallelogram connected to the main frame, a first supporting arm connected to the linkage parallelogram, an energy storing element connected to the linkage parallelogram at a plurality of places, and a mechanism for displacing the center of gravity of the apparatus. The displacing mechanism includes a second supporting arm having a first non-vertical axis (A—A) which is rotatably connected to the first supporting arm and which is connected to the apparatus at a connection point. The connection point has a second non-vertical axis which is perpendicular to the first non-vertical axis. The displacing mechanism displaces the center of gravity of the apparatus into a point of intersection of the first non-vertical axis and the second non-vertical.

BRIEF DESCRIPTION OF THE DRAWINGS

Illustrative embodiments of the present invention are diagrammatically represented in the drawings. In the drawings:

FIG. 1b shows, in top plan view, that which is shown in FIG. 1a;

FIG. 3 shows a ground stand with a linkage parallelogram rod system and an accessory device according to the invention;

DETAILED DESCRIPTION OF THE PREFERRED EMBODIMENTS

Figure 1A:
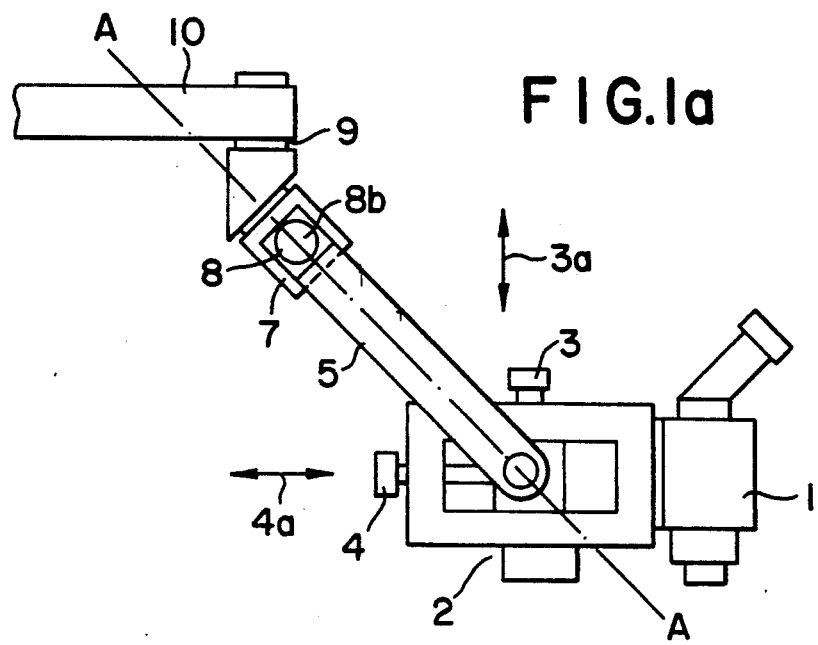
FIG. 1a shows a part of a stand suspension with attached operating microscope in side view.
Figure 1B:
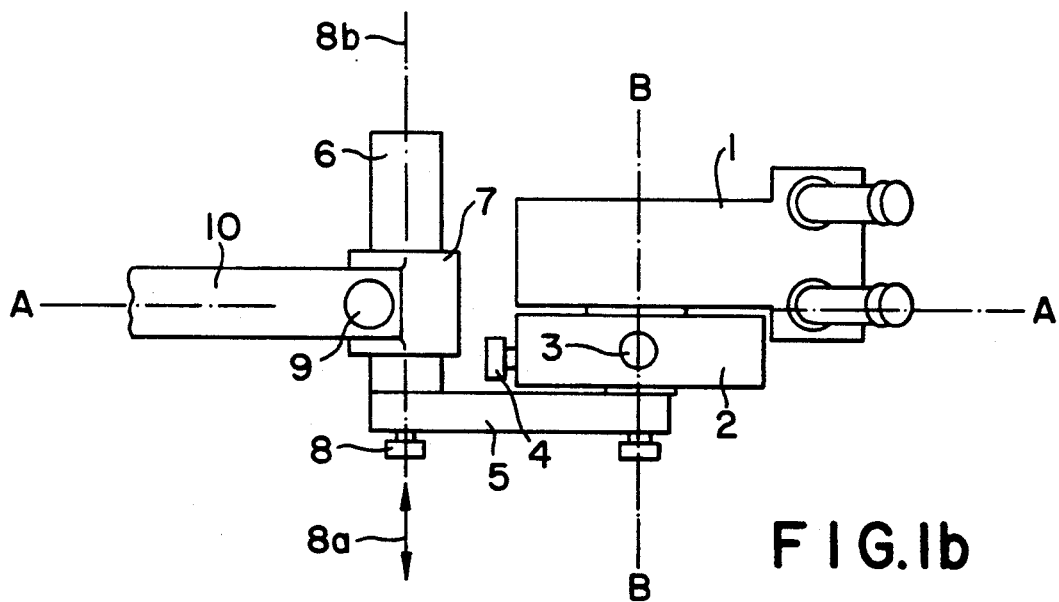
Figure 2:
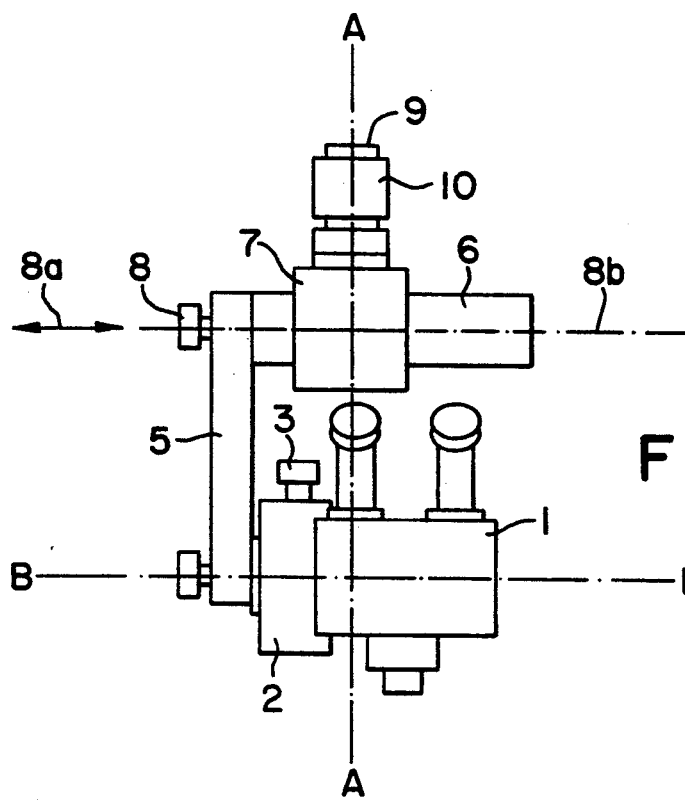
FIG. 2 shows the representation of FIG. 1 in front view.

FIG. 1a shows an apparatus, for example an operating microscope, bearing the reference numeral 1, which apparatus is adapted to a supporting device 2, which is articulated to the lower end of a supporting arm 5. The supporting arm 5 is connected, in its upper part, with a carriage 6 which can be displaced in a guide 7 along the translation axis 8b, i.e. in the direction of the double arrow 8a, by means of the spindle 8. The described suspension is rotatably connected to a supporting arm 10 by means of a rotary bearing 9. The supporting device 2 exhibits two assemblies, which can be finely adjusted by means of the adjusting devices 3 and 4 respectively in the direction of the double arrow 3a and 4a respectively. It is evident from the representation of the directions of displacement 3a, 4a and 8a respectively in FIGS. 1 and 2 that the apparatus 1 car: be displaced in three spatial coordinate directions which are perpendicular to one another, in a controlled manner. FIGS. 1a and 1b show, by A—A, a non-perpendicular axis which extends parallel to the supporting arm 5 and is perpendicular to the horizontal (non-vertical) axis B—B. The point of intersection of the two axes A—A, B—B is shown in FIG. 2. The axis B—B extends through the linkage axis at the lower end of the supporting arm 5, about which linkage axis the apparatus 1 can be tilted.

The equilibrium condition for the apparatus 1 or for the overall system is now created in that the center of gravity of the system is brought by means of displacements along the three spatial directions (3a; 4a; 8a) into the point of intersection of the two non-perpendicular axes A—A, B—B.

In FIG. 3, there is in the upper part of a ground stand 16 a linkage parallelogram 18 which exhibits a plurality of rods which are connected to one another by means of linkages 12a–12d. Moreover, a plate 20 is shown, which exhibits inter alia the linkage 12b. An energystoring element 11, known per se—for example a compressed-gas spring—is connected on the one hand to the upper rod of the parallelogram and on the other hand to the plate 20. This energy-storing element 11 applies the required counterbalancing force which is required for the setting of an equilibrium condition upon alteration of the so-called elevation, i.e. in the vertical direction. In order to permit the properties of easy, rapid and secure orientation, it is required to provide on the linkages 12a–12d of the linkage parallelogram 18 constructive measures to reduce the linkage friction which permit the effect of an—in this case negative—property of the energy-storing elements, namely the changing energy as a function of the vertical movement. Since the vertical movement of the energy-storing element 11 is dependent upon the angular position of the linkage parallelogram 18, a compensation of the verticalmovement-dependent change of energy is necessary in the case of a reduced linkage friction, since otherwise the equilibrium can be set at the linkage parallelogram, when the energy-storing element 11 has been incorporated, only for a single angular position of the parallelogram and thus only for a specified height.

Figure 4:
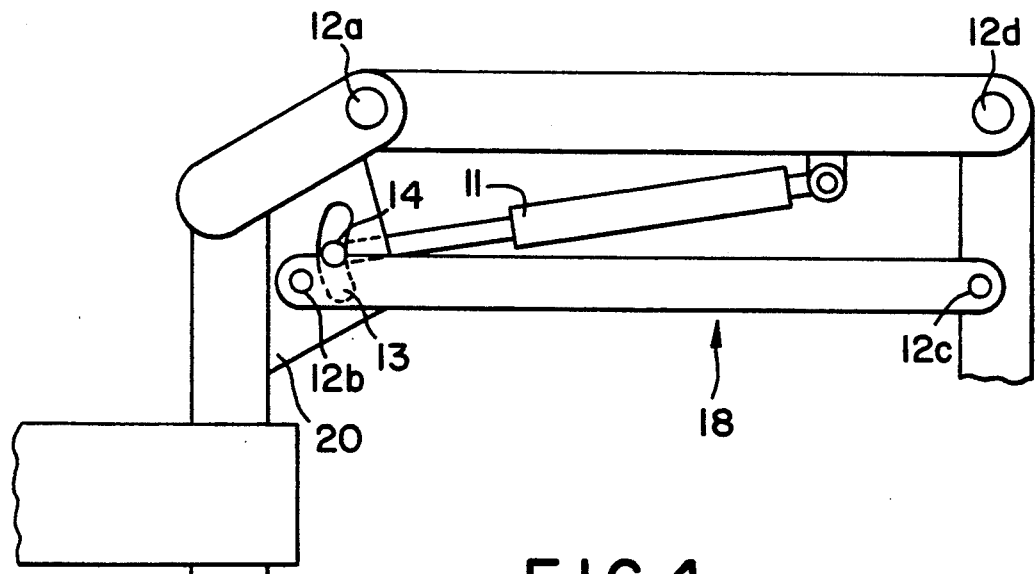
FIG. 4, shows a detail view of the linkage parallelogram rod system together with another accessory device according to the invention.
Figure 5:
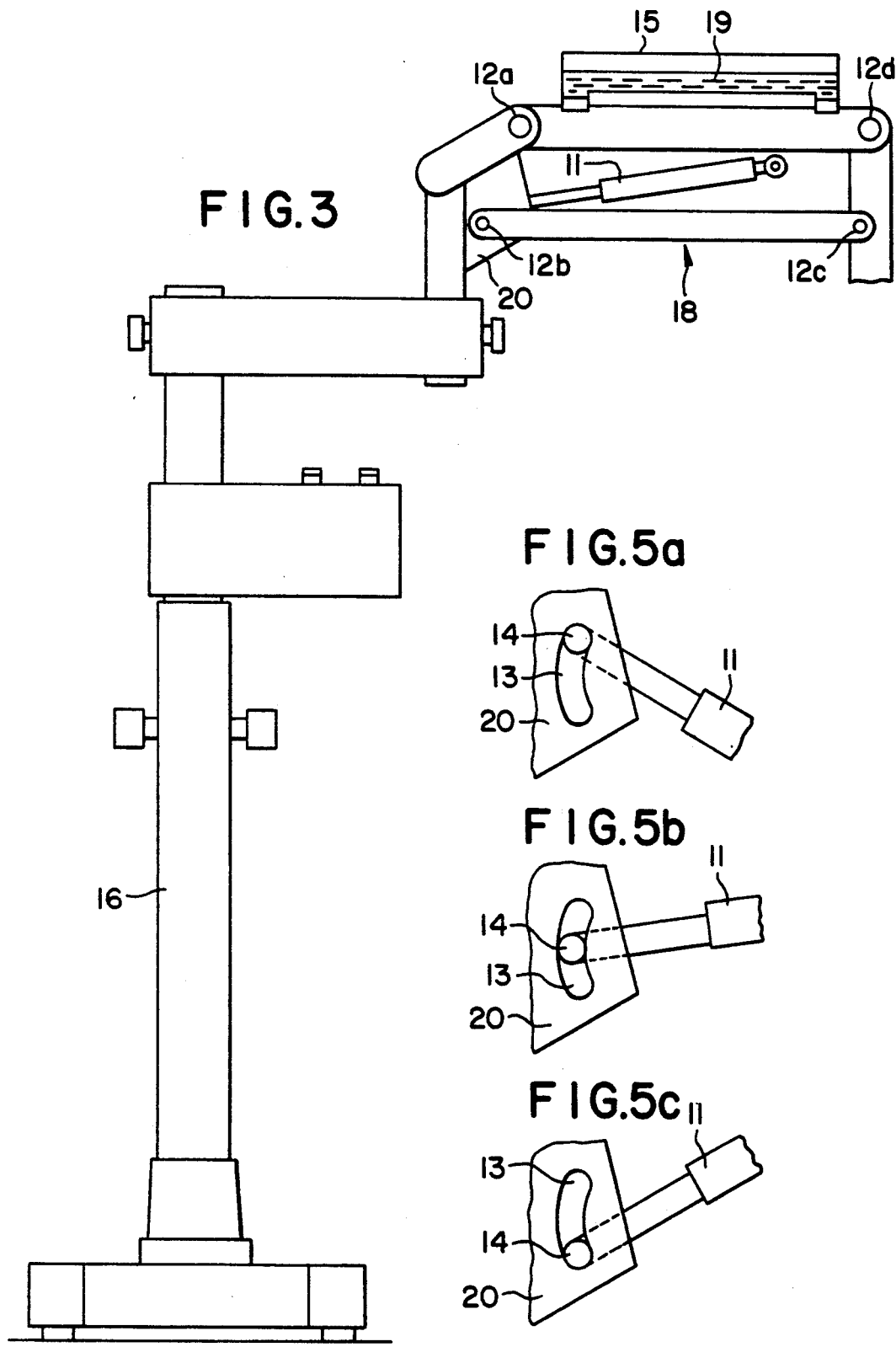
FIGS. 5a-5c show diagrammatic detail views of FIG. 4 regarding the different positions of a component as a function of the elevation of the (optical) apparatus.
Figure 6:
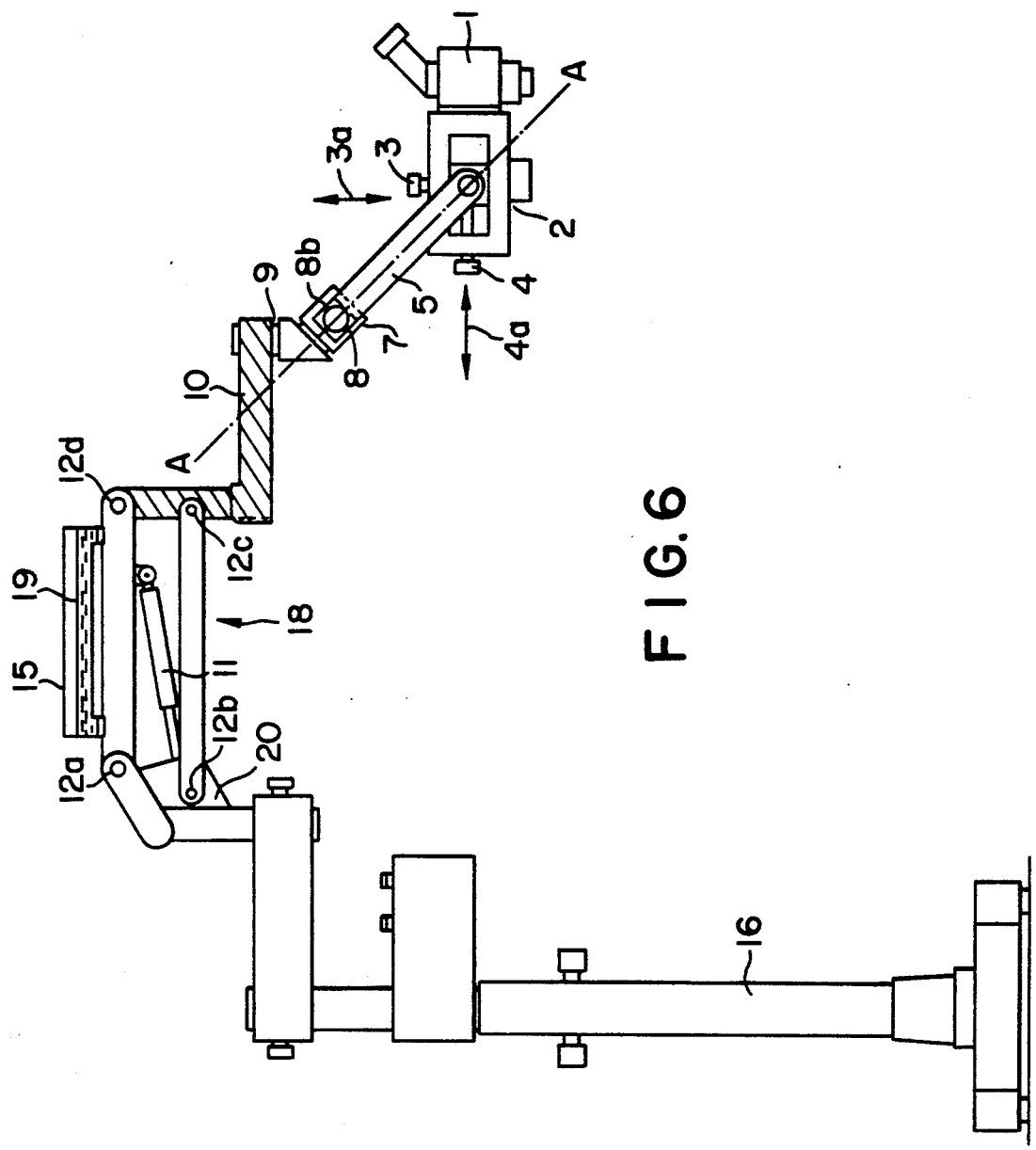
FIG. 6 shows a stand suspension including the structure of FIGS. 1a and 3.

This compensation of the changing energy is effected by an additional component according to the invention for the linkage parallelogram. This is explained in greater detail in FIGS. 4 and 5a–5c. The required compensation of the changing energy is achieved by an angle-dependent alteration of position of the suspension of the energy-storing element 11 in the plate 20. As can be seen from FIG. 4, the compressed-gas spring 11 engages via a pin 14 into a slot 13. The slot is designed as a circular-arcuate elongate hole and ensures the guiding of the pin 14 as a function of the elevation of the linkage parallelogram 18. The length of the slot is determined according to the energy changes—which are to be compensated—of the energy-storing element 11. The slot effects a continuous guiding of the pin 14 from one end to the other in the course of the movement of the linkage parallelogram 11. FIG. 5a shows that at maximum lowering (reduction of the elevation) of the linkage parallelogram the pin 14 comes to lie in the upper end-stop region of the slot 13, while this lies in the lower end-stop region of the slot 13 at maximum elevation - cf. FIG. 5c. FIG. 5b shows the middle position, as is evident, for example, from FIG. 4 (horizontal extent of the two rods of the linkage parallelogram 18).

The function of this accessory device according to the invention is the following: the pivot arm or the linkage parallelogram 18 is operated during the operation in the course of the setting of the height of the microscope (elevation). The energy-storing element 11, in this case the compressed-gas spring, has an energy which acts in the direction of its suspension in the plate 20 (i.e. in the direction towards the pin 14). The length of the perpendicular between this energy direction and the linkage 12a is that lever arm which is of decisive importance as to the question of whether the pivot arm or the linkage parallelogram 18 does or does not remain in the once set elevation (suspension). In the active position, the linkage parallelogram 18 can be moved from the horizontal through approximately 35° upwardly (cf. FIG. 5c) and downwardly (cf. FIG. 5a). In the raised position, the compressed-gas spring 11 is completely extended; in the lowered position, it is completely drawn in. As a function of this extension of the compressed-gas spring 11, the energy thereof alters. In the upper position of the linkage parallelogram 18, the energy of the compressed-gas spring 11 is weaker; in the lower position of the linkage parallelogram 18, the energy of the compressed-gas spring 11 is stronger. Accordingly, this means that with an identical lever arm the energy changes. In the case of the known pivot arms or linkage parallelograms according to the prior art, this change has been masked or "concealed" by the setting of the friction linkages 12a–12d. However, if for supervening reasons of a modern handling convenience, a lowering of the linkage friction specifically of these linkages 12a–12d must be undertaken, this automatically leads to a situation in which the described energy changes now fully develop their effects: if the linkage parallelogram 18 was balanced out in a middle position, then the energy reduction of the compressed-gas spring 11 caused, in the upper position of the linkage parallelogram 18, a falling down and the energy increase in the lower position of the linkage parallelogram 18 caused an independent rise of the linkage parallelogram. Accordingly, it was necessary to undertake an alteration of the lever arm as a function of the linkage parallelogram position. This is achieved with the curved slot guidance, executed in the plate 20, for the suspension of the energy-storing element 11. When the pivot arm has been lowered, the pin 14 moves upwardly in the curve, so that the lever arm becomes shorter and the energy is no longer sufficient to press the pivot arm independently upwardly. On the other hand, when the pivot arm has been raised the exact opposite follows: the pin 14 moves downwardly, so that the lever arm becomes greater and the energy is sufficient to hold the pivot arm up. Although the slot 13 has been shown as part of a circular arc, other curve designs are in principle also possible.

In place of this described measure according to the invention, in the case of a further embodiment of the present invention it is possible to achieve a compensation of the changing energy in that the weight force to be balanced by the energy-storing element 11 increases continuously in the course of the movement of the linkage parallelogram 18, and specifically in such a manner that this increase counteracts the increasing energy of the energy-storing element 11. In this connection, reference is made to FIG. 3, in which the linkage parallelogram 18 is shown with a conventionally suspended energy-storing element 11. The energy-storing element 11 shown has been incorporated into the linkage parallelogram 18 in such a manner that in the case of a downwardly pointing parallelogram the vertical-movement-dependent energy increases. To compensate this, it is possible to fit a liquid container 15 onto a rod of the linkage parallelogram 18—preferably onto the upper one. In the case of a downwardly pointing parallelogram, the necessary increase in weight force is then achieved in a simple manner by displacement of the liquid in the not entirely filled liquid container 15. It is within this invention proposal to provide either containers of differing spatial form or differing degree of filling or differing container liquid, in order to be able to achieve all required compensating (counterbalancing) forces. Naturally, it is also possible to connect the liquid container 15 to an internal fluid-regulation circuit system for the controllable infeed and removal of liquid situated in a separate reservoir.

The proposed solutions according to the invention have made possible a low-effort as well as a very precise orientation of the microscope in height over the field of operation. This leads to a more intense concentration of the surgeon carrying out, for example, a micro-operation on his actual main task, and thus to a shortening of the total manipulation in vivo.

| List of Reference Symbols | |
|---|---|
| 1 | Apparatus (for example, Operating microscope) |
| 2 | Supporting device |
| 3; 4 | Adjusting devices (spindle drives) |
| 3a; 3b | Double arrows (translation direction indicators) |
| 5 | Supporting arm |
| 6 | Carriage |
| 7 | Guide |
| 8 | Spindle |
| 8a | Double arrow (translation direction indicators) |
| 8b | Translation axis of (6) and (7) |
| 9 | Rotary bearing |
| 10 | Supporting arm |
| 11 | Energy-storing element (Compressed-gas spring) |
| 12a, 12b, 12c, 12d | Linkages |
| 13 | Slot |
| 14 | Pin |
| 15 | Liquid container |
| 16 | Ground stand |
| 18 | Linkage parallelogram |
| 19 | Liquid |
| 20 | Plate |
| A-A | (first) non-vertical axis |
| B-B | (second) non-vertical axis |

We claim:

1. A stand for supporting an apparatus, comprising:
   a main frame;
   a linkage parallelogram connected to said main frame;
   a first supporting arm connected to said linkage parallelogram;
   an energy storing element connected to said linkage parallelogram at a plurality of places; and
   means for displacing the center of gravity of said apparatus including a second supporting arm having a first non-vertical axis (A—A), said second supporting arm being rotatably connected to said first supporting arm and being connected to said apparatus at a connection point having a second non-vertical axis (B—B) which is perpendicular to said first non-vertical axis;
   wherein said displacing means displaces the center of gravity of said apparatus into a point of intersection of said first non-vertical axis and said second non-vertical axis.

2. A stand as recited in claim 1, further comprising a mechanism for varying the location of one of the plurality of places in response to a corresponding movement of said linkage parallelogram, and wherein said displacing means further comprises
   (a) a supporting device having first and second assemblies, and first and second adjustment devices operatively connected to said first and second assemblies, respectively, such that said first and second assemblies are displaceable relative to each other, and wherein said apparatus being secured to said first assembly, said second supporting arm being connected in an articulating manner to said second assembly, and said first and second assemblies being displaceable in first and second directions, respectively, said first and second directions being substantially perpendicular to each other; and
   (b) a guiding device connected to an upper region of said second supporting member, said guiding device including a guide, a carriage which is displaceable in said guide, and a spindle for displacing said carriage within said guide and along a translational axis which is perpendicular to said first and second directions;

wherein said mechanism varies the location of one of the plurality of places in response to said corresponding movement of said linkage parallelogram such that a substantially constant force is exerted by said energy-storing element on said linkage parallelogram regardless of the position of said linkage parallelogram.

3. A stand as recited in claim 2, wherein said first and second adjustment devices each include a spindle drive.

4. A stand is recited in claim 2, wherein said first and second adjustment devices and said spindle each extend along a nonlinear path.

5. A stand as recited in claim 4, wherein said non-linear path is spherical.

6. A stand as recited in claim 2, wherein said mechanism includes a plate which has a circular arcuate slot and which is connected to said linkage parallelogram, and a pin which is rigidly connected to said energy-storing element and which is guided within said slot without play so that it acts as a bearing axis.

7. A stand as recited in claim 6, wherein said slot deviates from a circular contour and is non-linear.

8. A stand as recited in claim 1, wherein said linkage parallelogram reducing a linkage friction during movement of said linkage parallelogram.

9. A stand as recited in claim 1, further comprising a container which is at least partially filled with a liquid and which is connected to said linkage parallelogram so that when said linkage parallelogram is raised or lowered there is a variation in a force produced by said energy storing device which acts on said linkage parallelogram and said liquid is displaced in said container to counterbalance said variation.

10. A stand as recited in claim 2, wherein said container is releasably connected to said linkage parallelogram and is a closed system.

* * * * *